United States Patent [19]

Puvvada

[11] Patent Number: 5,965,500
[45] Date of Patent: Oct. 12, 1999

[54] STABLE LIQUID COMPOSITION COMPRISING HIGH LEVELS OF EMOLLIENTS

[75] Inventor: Sudhakar Puvvada, Rutherford, N.J.

[73] Assignee: Levers Brothers Company, Division of Conopco, Inc., New York, N.Y.

[21] Appl. No.: 08/899,101

[22] Filed: Jul. 24, 1997

[51] Int. Cl.⁶ .............................. C11D 7/50; C11D 17/00; A61K 7/50; A61K 7/48
[52] U.S. Cl. .................. 510/130; 510/135; 510/153; 510/155; 510/159; 510/156
[58] Field of Search ..................................... 510/130, 125, 510/127, 129, 135, 159, 153, 155, 156

[56] References Cited

U.S. PATENT DOCUMENTS

| | | | |
|---|---|---|---|
| 3,829,563 | 8/1974 | Barry et al. ................................ | 424/70 |
| 4,673,525 | 6/1987 | Small et al. .............................. | 252/132 |
| 5,234,619 | 8/1993 | Greene et al. ........................... | 252/108 |
| 5,308,526 | 5/1994 | Dias et al. ............................... | 252/108 |
| 5,409,640 | 4/1995 | Giret et al. ............................... | 252/546 |
| 5,776,872 | 7/1998 | Giret et al. ............................... | 510/124 |

*Primary Examiner*—Mark Kopec
*Assistant Examiner*—John M Petruncio
*Attorney, Agent, or Firm*—Ronald A. Koatz

[57] ABSTRACT

The present invention provides high foaming aqueous liquid compositions with levels of oil/emollient equal to or in excess of level of surfactant. It is surprising that good levels of foam can be maintained at such high levels of emollient. In addition to surfactant and emollient, compositions also preferably comprise $C_{12}$-$C_{24}$ fatty acid and/or cationic polymer.

9 Claims, No Drawings

STABLE LIQUID COMPOSITION COMPRISING HIGH LEVELS OF EMOLLIENTS

FIELD OF INVENTION

The present invention relates to liquid cleansing compositions of the type typically used in skin cleaning or shower gel composition. In particular, the invention relates to liquid compositions comprising high levels of emollients, especially where levels of emollients equal or exceed level of the total surfactant.

BACKGROUND

Liquid cleansers and shower gels are well known in the art. The use of such aqueous liquid cleansers with moisturizers is also known (see U.S. Pat. No. 5,308,526 to Dias et al. or U.S. Pat. No. 5,234,619 to Greene et al, for example).

In U.S. Pat. No. 5,234,619 to Greene et al., for example, it is taught that moisturizers may be included at levels up to about 20% and among moisturizers taught are included petrolatum, mineral oil, silicones and various animal or vegetable oils (see claim 3, lines 8–28).

In these and other references of which applicants are aware, however, the level of oil/emollient used is always below the level of surfactant used. Applicants are aware of no reference in which the level of oil/emollient is equal to or greater than the amount of total surfactant.

BRIEF DESCRIPTION OF THE INVENTION

Suddenly and unexpectedly, applicants have found that compositions comprising an amount of oil/emollient equal to or in excess of surfactant provide mild, cleansing compositions which still maintain good lather and other desirable consumer benefits.

Specifically, the invention relates to aqueous liquid compositions comprising:

(1) 3 to 30%, preferably 10 to 25% by weight surfactant, particularly surfactant systems comprising mixture of anionic and amphoteric or zwitterionic surfactants; and (2) 10 to 35%, preferably 10–30% oil or emollient, wherein level of oil/emollient is equal to or in excess of total level of surfactant. Preferably, the compositions have viscosity of 50,000–300,000 cps measured using a Brookfield Viscometer with a helipath accessory and a T-bar spindle A at 0.5 RPM (measured at room temperature).

In preferred embodiments, the composition further comprises 0 to 10%, preferably 0.1 to 8%, more preferably 0.1 to 4% by weight $C_2$-$C_{24}$ fatty acid and/or 0.01 to 5%, preferably 0.01 to 3% cationic polymer conditioner.

DETAILED DESCRIPTION OF INVENTION

The present invention relates to aqueous cleanser or shower gel compositions comprising surfactant systems and emollient/oils wherein level of oil/emollient equals or is in excess of level of surfactant. Using compositions of invention, it is possible to obtain a high lathering, ultramild body wash that is stable and does not phase separate into oil rich and surfactant rich phases. Large amounts of foam are generated even at high levels of oil while the oil simultaneously counters skin irritation and dryness. Compositions are set forth in greater detail below.

Surfactants

The surfactant system of the subject invention comprises 3% to 30%, preferably about 10 to 25% surfactant, when at least one surfactant is anionic surfactant.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula

$$R^4CONHCH_2CH_2O_2CCH_2CH(SO_3M)CO_2M$$

wherein $R^4$ ranges from $C_8$-$C_{22}$ alkyl and M is a solubilizing cation;

amido-MIPA sulfosuccinates of formula

$$RCONH(CH_2)CH(CH_3)(SO_3M)CO_2M$$

where M is as defined above.

Also included are the alkoxylated citrate sulfosuccinates; and alkoxylated sulfosuccinates such as the following:

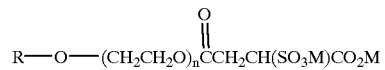
$$R\text{---}O\text{---}(CH_2CH_2O)_n\overset{\overset{O}{\|}}{C}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

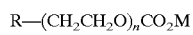
$$R\text{---}(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine $LCQ^{(R)}$ by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate, if used, may be an alkoxylated isethionate such as is described in Iliardi et al., U.S. Pat. No. 5,393,466, hereby incorporated by reference into the subject application. This compound has the general formula:

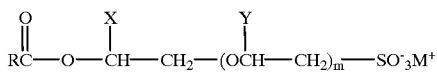

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 20% by weight of the composition, preferably 2 to 15%, most preferably 5 to 12% by weight of the composition.

In a preferred embodiment of the invention, there is at least one anionic which should be used in combination with a zwitterionic or amphoteric surfactant.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

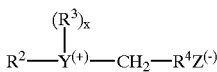

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

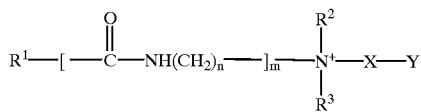

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

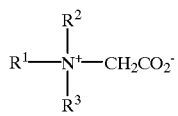

and amido betaines of formula:

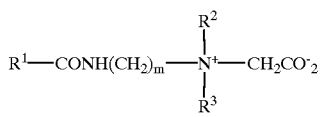

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

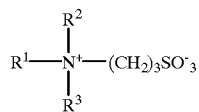

or

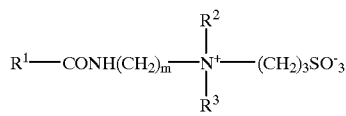

where m is 2 or 3, or variants of these in which —(CH$_2$)$_3$SO$^-$$_3$ is replaced by

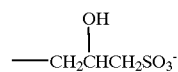

In these formulae R$^1$, R$^2$ and R$^3$ are as discussed previously.

Amphoacetates and diamphoacetates are also intended to be covered in possible zwifterionic and/or amphoteric compounds which may be used.

The amphoteric generally should comprise about 0.1 to 20%, preferably 5 to 15% of the composition.

As noted, total surfactant should not exceed about 30% of composition.

A particularly preferred system comprises about 5 to 15% anionic, particularly 5 to 15% alkali metal C$_8$-C$_{16}$ ether sulfate (e.g., sodium lauryl ether sulfate) and about 5 to 15% amphoteric selected from the group consisting of amphoacetates (e.g., sodium lauroamphoacetate) or amidoalkylbetaine (e.g., cocoamido propylbetaine).

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl (C$_6$-C$_{22}$) phenols-ethylene oxide condensates, the condensation products of aliphatic (C$_8$-C$_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Lienado, both of which are also incorporated into the subject application by reference.

Preferred alkyl polysaccharides are alkylpolyglycosides of the formula

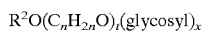

wherein R$^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

Oil/Emollient

The present invention also comprises an amount of oil/emollient required to equal or be in excess of the amount of total surfactant.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and sunflower seed oil.

Esters: Butyl myristate, cetyl palmitate, decyl oleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Lanolin alcohols, acytylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

Particularly preferred emollients include vegetable oils, particularly sunflower seed. In a preferred embodiment of the invention, sunflower seed oil comprises at least about 20% by weight of the composition.

Emollient will generally comprise 10% to 35%, preferably 10% to 30% of composition.

In a preferred embodiment of the invention, the composition will comprise a fatty acid "structurant" which helps to form a lamellar phase (lamellar phase composition being particularly preferred). The structurant helps to suspend emollient while maintaining good shear thinning properties.

The fatty acid is generally a C$_{12}$-C$_{24}$ fatty acid. A particularly preferred fatty acid is lauric acid. Other preferred fatty acids include but are not limited to palm kernel acid, palm fatty acid and isostearic acid. The acid will comprise 0% to 10%, preferably 0.1% to 8%, more preferably 0.1 to 4% of the composition.

In another preferred embodiment, the composition will comprise a cationic conditioners. Examples of such polymers include Quatrisoft LM-200, Polyquaternium-24, Polyquaternium 39 from Calgon, and Jaguar$^{(R)}$ type cationic polymers from Rhone Poulenc. Generally, this will comprise 0.01% to 3% of the composition.

Finally, water will comprise balance of composition. Water generally comprises greater than about 30%, preferably greater than about 40% by weight of the composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil$^{(R)}$ from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Thickeners which may be used include Amerchol Polymer HM 1500 (Nonoxynyl Hydroethyl Cellulose); Glucam DOE 120 (PEG 120 Methyl Glucose Dioleate); Rewoderm $^{(R)}$ (PEG modified glyceryl cocoate, palmate or tallowate) from Rewo Chemicals; Antil$^{(R)}$ 141 (from Goldschmidt).

Another optional ingredient which may be added are the defloculating polymers such as are taught in U.S. Pat. No. 5,147,576 to Montague, hereby incorporated by reference.

Another ingredient which may be included are exfoliants such as polyoxyethylene beads, walnut sheets and apricot seeds The compositions of the invention generally will have viscosity of about 50,000 to 300,000 centipoises (cps) measured using a Brookfield Viscometer with a helipath accessory and a T-bar spindle A at 0.5 RPM (measured at room temperature).

The invention will now be described in greater detail by way of the following non-limiting examples. The examples are for illustrative purposes only and not intended to limit the invention in any way.

All percentages in the specification and examples are intended to be by weight unless stated otherwise.

EXAMPLES

The following examples of composition of the invention are set forth below:

| INGREDIENTS | I | II | III | IV | V |
|---|---|---|---|---|---|
| SURFACTANTS | 15 | 17.5 | 17.5 | 17.5 | 17.5 |
| Cocoamido Propyl Betaine | 0 | 10.5 | 10.5 | 0 | 0 |
| Sodium Lauroamphoacetate | 10 | 0 | 0 | 10.5 | 8.75 |
| Sodium Laureth Sulfate | 5 | 7 | 7 | 7 | 8.75 |
| EMOLLIENTS | 15 | 35 | 35 | 25 | 26 |
| Dimethicone | 0 | 0 | 0 | 0 | 2 |
| Sunflower seed Oil | 15 | 30 | 30 | 20 | 21 |
| Glycerine | 0 | 5 | 5 | 5 | 3 |
| Petrolatum | 0 | 0 | 0 | 0 | 0 |
| Lanolin Alcohol | 0 | 0 | 0 | 0 | 0 |
| FATTY ACID | | | | | |
| Lauric acid | 2.5 | 0 | 0 | 2.6 | 2.6 |
| Isostearic Acid | 0 | 5 | 5 | 0 | 0 |
| OTHER INGREDIENTS | | | | | |
| Citric Acid | 0.8 | 0 | 0 | 1 | 1 |
| Magnesium Sulfate | 1.5 | 0 | 0 | 1 | 0.4 |
| Guar Hydroxypropyl-trimonium Chloride | 0 | 0.5 | 1.5 | 1 | 0.5 |
| Polyquaternium 37/ Propylene Glycol | 0 | 0.1 | 0.2 | 0 | 0 |

-continued

| INGREDIENTS | I | II | III | IV | V |
|---|---|---|---|---|---|
| Dicaprylate Dicaprate/ PPG1 Tridecth 6 | | | | | |
| PEG 20 Sorbiton Monolaurate | 0 | 0 | 2 | 0 | 0 |
| PEG 80 Sorbiton Monolaurate | 0 | 0 | 0 | 4 | 0 |
| Fragrance | 1.0 | 1.0 | 1 | 1 | 1 |
| Miscellaneous | 0–1 | 0–1.0 | 0–1 | 0–1.0 | 0–1.0 |
| Water | to 100.0 | to 100.0 | to 100.0 | to 100.0 | to 100.0 |

Compositions I–V were prepared as follows

Surfactants were mixed at 150–180° F. with deionized water followed by addition of citric acid and/or magnesium sulfate, emollient oils, fatty acids, preservatives and antioxidants. In examples I, IV–V, the fatty acid was dissolved in the sunflower seed oil and the oil premix added. Perfumes were added at about 100–120° F. as the batch was being cooled.

As can be seen in every example, the oil or emollient is equal to or exceeds level of surfactant.

I claim:

1. An aqueous liquid composition comprising:
    (a) 3 to 30% by weight surfactant system comprising a surfactant selected from the group consisting of anionic, amphoteric, cationic and nonionic surfactants and mixtures thereof, wherein at least one anionic surfactant must be present; and
    (b) 10 to 35% by weight of an oil/emollient selected from the group consisting of vegetable oils, esters, animal fats, mineral oil, petrolatum, silicone oil and mixtures thereof, wherein the level of oil/emollient is equal to or in excess of level of surfactant;
    (c) 0.1 to 8% by wt. $C_{12}C_{24}$ fatty acid;
    (d) 0.01 to 3% by wt. cationic polymer; and
    (e) greater than 30% by weight water;
wherein said composition is in a lamellar phase; and
wherein said composition has a viscosity of 50,000 to 300,000 cps.

2. A composition according to claim 1, wherein surfactant system comprises mixture of anionic and amphoteric surfactants.

3. A composition according to claim 2, wherein anionic surfactant is an alkali metal, $C_8$-$C_{16}$ ether sulfate.

4. A composition according to claim 2, wherein amphoteric surfactant is selected from the group consisting of amphoacetates and amidoalkyl betaines.

5. A composition according to claim 2, wherein anionic is alkali metal $C_8$-$C_{16}$ ether sulfate and amphoteric is selected from the group consisting of amphoacetates and amidoalkylbetaines.

6. A composition according to claim 1, wherein said vegetable oil is sunflower seed oil.

7. A composition according to claim 1, wherein fatty acid is lauric acid.

8. A composition according to claim 1, wherein fatty acid is palm kernel acid, palm fatty acid or isostearic acid.

9. A composition according to claim 1, comprising 10 to 25% surfactant.

* * * * *